United States Patent
Selm et al.

(10) Patent No.: US 7,866,177 B2
(45) Date of Patent: Jan. 11, 2011

(54) PERSONAL COOLING ELEMENT, IN PARTICULAR FOR PATIENTS

(75) Inventors: Bärbel Selm, Berg/SG (CH); Benno Wüst, Thal (CH); Markus Weder, Flawil (CH)

(73) Assignee: UNICO Swiss tex GmbH, Alpnachstad (CH)

( * ) Notice: Subject to any disclaimer, the term of this patent is extended or adjusted under 35 U.S.C. 154(b) by 1030 days.

(21) Appl. No.: 10/588,472

(22) PCT Filed: Feb. 1, 2005

(86) PCT No.: PCT/CH2005/000051

§ 371 (c)(1),
(2), (4) Date: Jan. 17, 2007

(87) PCT Pub. No.: WO2005/074846

PCT Pub. Date: Aug. 18, 2005

(65) Prior Publication Data

US 2008/0021529 A1    Jan. 24, 2008

(30) Foreign Application Priority Data

Feb. 5, 2004   (CH) .................................... 172/04

(51) Int. Cl.
*F25D 23/12* (2006.01)
(52) U.S. Cl. .................................................... 62/259.3
(58) Field of Classification Search ............... 62/259.3, 62/304; 607/96, 114

See application file for complete search history.

(56) References Cited

U.S. PATENT DOCUMENTS

| 3,017,888 | A | * | 1/1962 | Weiner | 607/104 |
| 3,212,286 | A | * | 10/1965 | Curtis | 62/259.3 |
| 5,269,369 | A | | 12/1993 | Faghri | |
| 5,433,083 | A | | 7/1995 | Kuramarohit | |
| 5,956,963 | A | * | 9/1999 | Lerner | 62/259.3 |
| 6,715,309 | B1 | * | 4/2004 | Junkins | 62/259.3 |
| 6,763,671 | B1 | * | 7/2004 | Klett et al. | 62/259.3 |

FOREIGN PATENT DOCUMENTS

| DE | 39 02 233 A | 8/1990 |
| EP | 0 885 601 A | 12/1998 |
| EP | 1 273 277 A2 | 7/2002 |
| GB | 2 248 675 A | 4/1992 |

\* cited by examiner

*Primary Examiner*—Melvin Jones
(74) *Attorney, Agent, or Firm*—Cohen Pontani Lieberman & Pavane LLP

(57) ABSTRACT

A personal cooling element for patients comprises at least one cooling zone (2) that can be pre-tensioned against the body surface (10) of a person wearing the personal cooling element. The cooling zone (2) is three-layered with an internal layer (4) that faces towards the body, an external layer (6) that faces away from the body and an evaporation zone (8) that is located therebetween. The internal layer (4) and the external layer (6) each are made from a material that is waterproof and permeable to water vapor. The evaporation zone (8) is supplied with liquid water.

20 Claims, 1 Drawing Sheet

PERSONAL COOLING ELEMENT, IN PARTICULAR FOR PATIENTS

This is a U.S. national stage of application No. PCT/CH2005/000051, filed on 1 Feb. 2005.

FIELD OF THE INVENTION

The invention relates to a personal cooling element, particularly for patients, according to the preamble of claim 1 and to a method for cooling of body parts according to the preamble of claim 10.

DISCUSSION OF THE RELATED ART

Numerous kinds of personal cooling elements, particularly cooling garments, are known in the art and have been designed for disparate applications. A good and efficient cooling of certain body parts is necessary for athletes as well as for workers who are exposed to hot heat sources, but also for patients in order to relieve disease symptoms and/or for therapeutic purposes.

U.S. Pat. No. 5,269,369 discloses a garment providing a thermal compensation between cooler and hotter thermal body parts of the wearing person. Heat is transferred through heat pipes from hotter body parts with a need for cooling to cooler body parts with a need for heating. The heat pipes are elastically formed and attached to the garment. However, the heat pipes of U.S. Pat. No. 5,269,369 can also be connected to an external cooling or heating element in order to achieve a selective cooling or heating of certain body parts. In U.S. Pat. No. 5,269,369 it is proposed to use such a garment not only in thermally extreme environments such as is the case, for example, when diving in considerable depths or in polar regions, but also for humans suffering form certain diseases, particularly multiple sclerosis (henceforth "MS").

To achieve a sufficient cooling effect for an extended time period with the garment described in U.S. Pat. No. 5,269,369 it is not sufficient to transfer heat from hotter body parts to cooler body parts through the heat pipes. Rather than that, a constant heat removal is necessary for a major part of the musculoskeletal system so that the heat pipes of U.S. Pat. No. 5,269,369 have to be connected to a heat sink that needs to be carried along. Such a garment is very heavy and thus only suitable for strong persons. Therefore, a use by children or elderly persons is not possible. Moreover, a permanent carrying along of the heat sink is cumbersome for the person wearing the garment and leads to restrictions in personal mobility.

EP 1,273,277 A2 discloses a garment for treating MS patients, wherein the garment comprises cooling elements in the form of tubes having a cooling effect at the internal side of the garment. Such a garment needs to be connected to a cooling device by means of connectors so as to transfer cooling medium to the cooling elements or away from these, respectively. Like the one of U.S. Pat. No. 5,269,369, this garment is heavy and uncomfortable due to its bulkiness and rigidity. For children, elderly persons and particularly also for patients, the cooling garment does not appear very useful. An embodiment in the form of a whole body garment, which would be desirable for certain applications, is barely feasible due to its large weight and its poor wearing comfort. Moreover, such a garment does not meet the requirements in respect of aesthetics due to its stiff structure and its bulkiness.

Further customary cooling methods for MS patients and also for other persons range from wet compresses to small portable ventilators. Although wet compresses are rather efficient, they lead to undesirable wetting of the person and of other clothing and thus are useful only in a few situations. Small ventilators and the like are not very effective, lead to a certain impairment of mobility and furthermore are unpleasant because of the noise. Particularly for patients with a temperature sensitive condition of the musculoskeletal system the known cooling devices and methods are not satisfactory for an active participation to social and professional life.

A further personal cooling element is disclosed in DE 39 02 233 A1. This is configured as a bag shaped cooling device to be filled with a cooling liquid and consists of a liquidproof, vapor permeable material that at the side thereof serving for cooling is in contact with the cooling liquid. Said material is coated on the side thereof not being in contact with the cooling liquid by a hydrophilic, water absorbing material layer and on top thereof by a hydrophobic, water conducting material layer, wherein all these materials are bielastic products. The hydrophobic, water conducting material layer is the layer arranged next to the body part to be cooled and serves to transport water from the body skin into the hydrophilic, water absorbing material layer. The cooling effect results primarily from the pool of cooling liquid, which typically has a temperature of −5 to 7° C. upon filling and thus forms a cold reservoir. An additional cooling effect moreover results from evaporation of the coolant. Coolant vapor exits from the bag by passing through the liquidproof, vapor permeable material and reaches the adjacent hydrophilic, water absorbing material layer and ultimately can escape into the surroundings. Therefore, the known personal cooling element is constructed as a kind of conventional hot-water bottle with the difference that coolant vapor can leave from the bag.

SUMMARY OF THE INVENTION

It is an object of the invention to improve a personal cooling element of the above mentioned type and to provide a method for cooling body parts.

These objects are achieved with the personal cooling element defined in claim 1 and by the method defined in claim 10.

The personal cooling element in accordance with one embodiment of the present invention comprises at least one cooling zone, wherein elastic means are provided to pretension the cooling zone against the body surface of a person wearing the personal cooling element. Due to the fact that the cooling zone is three-layered and has an internal layer facing towards the body, an external layer facing away from the body and an evaporation zone arranged therebetween, wherein the internal layer and the external layer each are made from material that is waterproof and permeable to water vapor, and wherein water supply means are present to supply the evaporation zone with liquid water, there results a personal cooling element that is compact, comfortable to wear, simply built and efficient.

Therefore, body parts to be cooled belonging to a person wearing the personal cooling element can be cooled by exploiting the evaporation energy of the water supplied to the evaporation zone. In the personal cooling element of the present invention the side intended for skin contact—also designated as internal layer in the present context—is not permeable for liquid water, in contrast to DE 39 02 233 A1. Therefore, the personal cooling element of the present invention stands out by having a substantially better wearing comfort compared to that in DE 39 02 233 A1 because the waterproof internal layer prevents wetting of the skin of the person that is wearing the personal cooling element. Such wetting would not only be unpleasant, but would also result in a loss of cooling water due to substantial take up of water by the skin. Moreover, the humidity released by the skin can be transported away to the outside, i.e. the body's cooling mechanism of sweating is still possible in spite of the cooling element lying above it. Due to the three-layered configuration with an evaporation zone arranged between the internal layer and the external layer, which evaporation zone can be supplied with water through the water supply means, the interstitial layer forming the evaporation zone can be very thin. The evaporation zone only needs to ensure that whenever there is a need for cooling some liquid water will be present—even if only in small amounts—so as to provide the necessary cooling by evaporation. By virtue of the fact that the external layer on the side of the evaporation zone facing away from the body can be substantially unobstructed and, in particular, is not overlaid by a bag-like reservoir such as in DE 39 02 233 A1, water vapor can easily escape through the external layer. This permits a comparably high evaporation rate and thus provides an excellent cooling power in spite of a very simple construction of the cooling element.

The personal cooling element in accordance with one embodiment of the present invention permits an efficient cooling of body parts and in this way can substantially improve the condition of the person wearing the personal cooling element. By virtue of the efficient cooling that is obtainable with simplest means, particularly MS patients can walk larger distances without a substantial loss of comfort and without pausing for exhaustion than without personal cooling element. In this way the quality of life of persons with certain conditions can be appreciably improved. On the other hand, the personal cooling element may also be used for performing certain athletic activities or work. In particular, the body's mechanism of cooling can be substituted or supplemented. In addition to water, which is a preferred coolant, it is also conceivable to use other water-based coolants such as a water alcohol mixture. In the present context the terms "waterproof", "not permeable for water" and "permeable to water vapor" shall be understood, accordingly, as impermeable or not permeable for the liquid mixture and as permeable to vapors of said mixture.

With the personal cooling element of the present invention an efficient cooling of selected body parts, particularly of extremities and muscle parts is possible. It is expected that the concomitant slight reduction of blood temperature results in a temperature reduction of the central nervous system, which results in an improved performance of MS patients.

Advantageously, the internal layer and external layer have a high heat conductivity. In order to ensure a tight skin contact of the cooling zone, the cooling zone can be provided, for example, with elastic bands. It is also possible to form the internal layer and/or the external layer as such from an elastically acting material. A tight fit of the cooling zone to the skin is imperative for an optimal cooling.

The internal layer can be made from a well hydrophobized tissue or as a membrane of polyetherester (for example Sympatex™) or from PTFE (for example Gore-Tex™). The external layer is advantageously made of a thin membrane of polyetherester (for example Sympatex™).

The method of cooling body parts in accordance with one aspect of the present invention is characterized in that the personal cooling element is brought into close contact with the skin of a body part to be cooled and is pre-tensioned against the same, and then the evaporation zone of the cooling zone is supplied with water continuously or intermittently, i.e. on demand. In this way a cooling of the body part being in thermal contact with the cooling zone is easily achieved by exploiting the evaporation energy of water. The cooling effect sets on rapidly and its duration can be controlled by the amount of supplied water: as soon as all the cooling water has evaporated, the cooling effect stops. In this way the dry personal cooling element can be kept on with good comfort also in phases without need for cooling.

The evaporation zone of the cooling zone can be made from various materials with different material properties. An embodiment according to which the evaporation zone is made of a hydrophilic material is particularly advantageous. In this way a good take-up and distribution of water is possible in this layer.

In order to further improve the take-up and distribution of water in the evaporation zone, an embodiment is advantageous in which the evaporation zone comprises a channel system. Advantageously, the latter covers the entire surface of the evaporation zone and is connected directly to an entrance opening for cooling water supplied thereto. Thus, the water can reach the channel system directly so as to achieve an optimum distribution of water in the evaporation zone. Advantageously, the external layer has a thickness of 1 to 5 µm. It has further turned out to be advantageous if the internal layer has a thickness of 10 to 20 µm.

In order to avoid a loss of the water supplied to the evaporation zone, the external layer and the internal layer are connected to form a lateral seal of the evaporation zone. In this way the whole evaporation zone is sealed from the outside by means of the internal layer and the external layer. Basically, supplied water can be lost only in the form of water via the external layer.

The personal cooling element can be formed, for example, as an elastic band but also as a garment. In particular, it can be very thin, for example like a stocking, and it is usually worn under normal clothing which, however, should ensure that evaporated water is removed as easily as possible. For a person suffering from a nervous or muscular disease it is preferable that the personal cooling element be formed as a thin elastic garment. In particular, this garment can be formed as whole body garment or as trousers and/or top. In this way it is possible to provide a cooling zone for large parts of the body surface and thus for a good cooling of the relevant body parts.

Furthermore, it can be advantageous to have the cooling zone formed to fit tightly to one or several selected body parts. In this way a specific cooling of heat sensitive body parts, particularly in case of local burns or sciatic nerve disease is possible.

An embodiment in which the water supply means comprise a water supply system connected to a pump is particularly advantageous. In this way a uniform distribution of the cooling liquid across the evaporation zone of the cooling zone may be achieved with minimum technical effort. As soon as the person wearing the personal cooling element is exposed to strong heat irradiation and/or becomes aware of a need for better cooling of the body, the person can supply coolant liquid to the cooling zone either automatically by means of an electrical pump or manually by means of a dispenser pump.

BRIEF DESCRIPTION OF THE DRAWING

An example of the invention will be described in detail by reference to the sole FIGURE that shows a section of a cooling zone of a personal cooling element worn tightly on the skin at the lower arm, in a cutaway view.

BRIEF DESCRIPTION OF THE PREFERRED EMBODIMENTS

Figure 1:
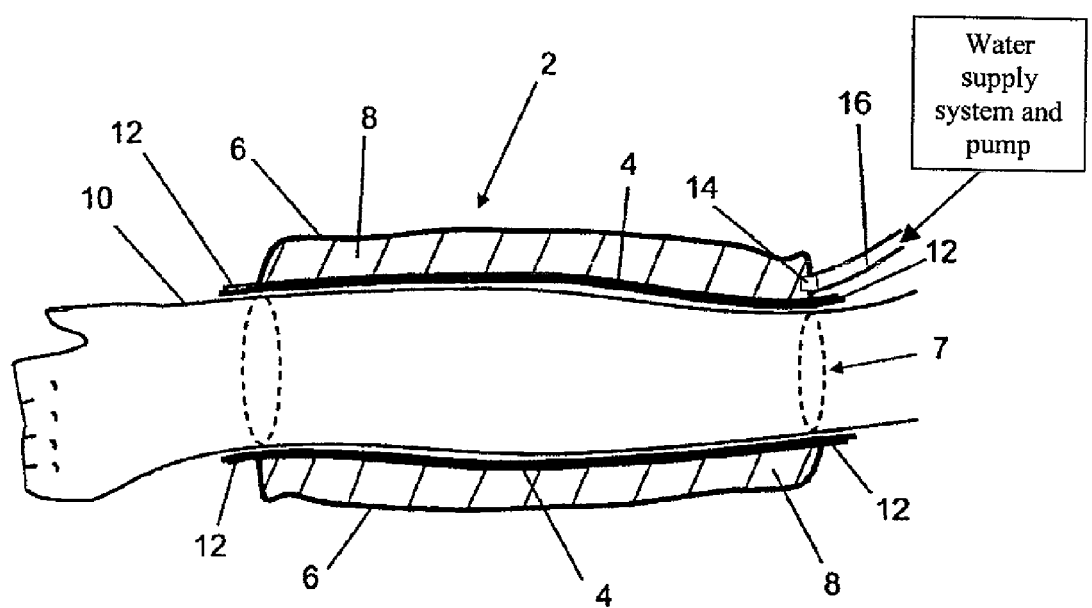

The three-layered cooling zone 2 shown in a cutaway view in the FIGURE is formed of a waterproof but water vapor permeable internal layer 4, a waterproof but water vapor permeable external layer 6 and a hydrophilic evaporation zone 8 arranged therebetween. The latter is provided for filling with water or a similar coolant and is preferably formed of a hydrophilic textile layer which is separated from the body surface 10 of a person wearing the personal cooling element by the internal layer 4. Preferably, the internal layer 4 as well the external layer 6 are each formed of an elastic membrane. The elastic layers 4, 6 act in a simple way as elastic pretensioning means 7 in order to ensure a tight fit of the cooling zone 2 to the skin. Alternatively, however, individual pre-tensioning means, i.e. pre-tensioning means that are independent of the internal and external layer, such as elastic bands, strings or the like can be used.

The internal layer 4 has a thickness of 10 to 20 μm in order to ensure a good heat conductance from the skin to the evaporation zone, on the one hand, and to avoid a passage of liquid water, on the other hand. At the same time the internal layer is permeable to water vapor, thus improving the wearing comfort of the cooling element and enabling the body's cooling effect of sweating. In the case of a Sympatex membrane with a layer thickness of 15 μm the water vapor passage resistance (Ret value) under dry conditions measured according to ISO 11092 is about 7 $m^2Pa/W$.

The external layer 6 has a thickness of about 1 to 5 micrometers and extends all the way to the lateral seals 12 of the evaporation zone in order to avoid the loss of water present in the evaporation zone 8. The external layer 6 is waterproof but highly permeable to water vapor and thus ensures an efficient removal of the water that has evaporated in the evaporation zone 8. In case of a Sympatex membrane with a layer thickness of 5 μm the Ret value under dry conditions is about 2 $m^2Pa/W$.

In an example of the personal cooling element the internal layer 4 facing towards the body is formed of a Sympatex membrane with a layer thickness of 15 μm, the external layer 6 facing away from the body is formed of a Sympatex membrane with a layer thickness of 5 μm and the evaporation zone 8 arranged between these layers is formed of a hydrophilic polyester sheet with a layer thickness of about 0.5 mm. For the three-layered arrangement in a dry state a Ret value of about 10 $m^2Pa/W$ was measured. Because in practical applications the evaporation rate of the coolant and accordingly also the cooling power are mainly limited by the passage of vapor from the hydrophilic middle layer to the external layer 6, it is primarily the Ret value of the external layer that matters, which has an advantageously low value of about 2 $m^2Pa/W$.

Water can be supplied to the evaporation zone 8 for example through an opening 16 by means of a flexible tube 14 and a pump not shown here. Advantageously, a small hand operated dispenser pump by means of which portions of a few milliliters of water can be supplied on demand is used for this task. Due to the hydrophilic properties of the evaporation zone 6 the water is distributed uniformly therein and thus provides for a uniform cooling of the body part that is covered by the cooling zone 2. Due to the evaporation of water and exit of water vapor through the external layer 6 heat is removed from the evaporation zone 8, which leads to a cooling of the corresponding body part due to the proximity of the evaporation zone 8 near the body and due to the good heat conductance of the internal layer 4.

Advantageously, the evaporation zone consists of a net-like web or another tissue with large effective surface in order to make the evaporation as efficient as possible.

The cooling element shown as a cutaway in the FIGURE can be used for cooling of smaller body parts, for example for patients with local burns, but also for the entire body. For a cooling of the entire body both the trousers and the top are formed completely like the cooling zone shown in the FIGURE as a cutaway. Both the trousers and the top then each form at least one cooling zone.

Various hydrophilic fiber materials can be used for the evaporation zone, with some polymeric fibers needing hydrophilization for using. Known methods for this purpose comprise, for example, a plasma treatment. Advantageously, the middle layer of the cooling element consists of an absorbent material that has good hydrophilic properties already by virtue of its yarn and construction.

In a test of the cooling ability of cooling trousers the addition of 15 g of water resulted in a reduction of the thigh's temperature by about 7° C. for a time period of one hour. The best cooling results were obtained with polyester materials that were very hydrophilic. These materials rapidly take up humidity over the surface and are capable to cause evaporation thereof in proximity of the skin. Already an additional displacement of 1 mm between the site of evaporation and the body surface would lead to a substantial loss in cooling effect and thus is very undesirable.

Because the heat conductivity between the evaporation zone facing away from the body and the body surface shall be as good as possible in order to effectively exploit the evaporation effect, the textile material as such, i.e. even in its dry state, should have a heat conductivity that is as high as possible and a heat insulation that is as small as possible, respectively. The Sympatex membranes used here have a heat conductivity of 0.048 W/mK in their dry state, which even rises to 0.244 W/mK, i.e. fivefold, in their wet state. The three-layered arrangement in the above example has a heat transfer resistance with a Rct value according to ISO 11092 of about $5.8 \times 10^{-3}$ $m^2K/W$. This value is substantially smaller than that of conventional underwear, which typically has Rct values of 25 to $30 \times 10^{-3}$ $m^2K/W$. If desired, an even better heat conductivity could be achieved by ion doping of the fibers.

For certain applications, for example for MS patients, it is desirable in practice to wear a piece of garment at least over parts of the cooling element. In this case it is advisable to use an outer garment that is loose fitting, i.e. not tight fitting. In this way, water vapor escaping from the cooling element is removed as efficiently as possible and thus further water vapor can follow. For this purpose, the permeability for water vapor of the external layer 6 should be as high as possible. Nevertheless, because the external layer 6 is not permeable to liquid water, a loss of liquid coolant, but also an undesirable wetting of the outer garment, are avoided.

An important field of application of the personal cooling element is the cooling of MS patients. In the field of high performance athletics it is possible to increase the efficiency of the athlete by means of the cooling effect of water evaporation because less sweat water needs to be produced for a given cooling. Finally, the personal cooling element is also suitable for workers who are exposed to a substantial heat impact.

The above described cooling element has been designated as "personal cooling element", but it could also be used for cooling of an animal body.

LIST OF REFERENCE NUMERALS 2 cooling zone
4 internal layer
6 external layer
7 elastic means
8 evaporation zone
10 body surface
12 lateral seal
14 water line
16 opening

The invention claimed is:

1. A personal cooling element, particularly for patients, with at least one cooling zone, wherein elastic means are provided to pre-tension the cooling zone against the body surface of a person wearing the personal cooling element, wherein the cooling zone is three-layered with an internal layer facing towards the body, an external layer facing away from the body and an evaporation zone arranged therebetween, wherein the internal layer and the external layer each are made from a material that is waterproof and permeable to water vapor, wherein water supply means are present to supply the evaporation zone with liquid water, and wherein the internal layer has a thickness of 10 to 20 μm.

2. A personal cooling element according to claim 1, wherein the evaporation zone is made from a hydrophilic material.

3. A personal cooling element according to claim 1 wherein the evaporation zone comprises a channel system.

4. A personal cooling element according to claim 1, wherein the external layer has a thickness of 1 to 5 μm.

5. A personal cooling element according to claim 1, wherein the internal layer and the external layer are connected to form a lateral seal of the evaporation zone.

6. A personal cooling element according to claim 1, wherein it is formed as a garment.

7. A personal cooling element according to claim 1, wherein the cooling zone is formed for a tight fit to at least one selected body part.

8. A personal cooling element according to claim 1, wherein the water supply means comprise a water supply system connected to a pump.

9. A method of cooling body parts by means of the personal cooling element according to claim 1, wherein personal cooling element is brought into close contact with the skin of a body part to be cooled and is pre-tensioned against the same, and that the evaporation zone is supplied continuously or intermittently with water.

10. A personal element according to claim 2, wherein the evaporation zone comprises a channel system.

11. A personal cooling element according to claim 3, wherein the external layer has a thickness of 1 to 5 μm.

12. A personal cooling element according to claim 3, wherein the internal layer and the external layer are connected to form a lateral seal of the evaporation zone.

13. A personal cooling element according to claim 4, wherein the internal layer and the external layer are connected to form a lateral seal of the evaporation zone.

14. A personal cooling element according to claim 1, wherein the internal layer and the external layer are connected to form a lateral seal of the evaporation zone.

15. A personal cooling element according to claim 3, the water supply means comprise a water supply system connected to a pump.

16. A personal cooling element according to claim 5, the water supply means comprise a water supply system connected to a pump.

17. A personal cooling element according to claim 6, the water supply means comprise a water supply system connected to a pump.

18. A personal cooling element, particularly for patients, with at least one cooling zone, wherein elastic means are provided to pre-tension the cooling zone against the body surface of a person wearing the personal cooling element, wherein the cooling zone is three-layered with an internal layer facing towards the body, an external layer facing away from the body and an evaporation zone arranged therebetween, wherein the internal layer and the external layer each are made from a material that is waterproof and permeable to water vapor, wherein water supply means are present to supply the evaporation zone with liquid water, and wherein the external layer has a thickness of 1 to 5 μm.

19. A personal cooling element according to claim 18, wherein the internal layer and the external layer are connected to form a lateral seal of the evaporation zone.

20. A personal cooling element according to claim 19, wherein the internal layer has a thickness of 10 to 20 μm.

* * * * *